(12) United States Patent
Kohlstruk et al.

(10) Patent No.: US 7,307,186 B2
(45) Date of Patent: Dec. 11, 2007

(54) MULTISTAGE CONTINUOUS PREPARATION OF CYCLOALIPHATIC DIISOCYANATES

(75) Inventors: Stephan Kohlstruk, Duelmen (DE); Manfred Kreczinski, Herne (DE); Rainer Elm, Marl (DE); Hans-Werner Michalczak, Herne (DE)

(73) Assignee: Degussa AG, Duesseldorf (DE)

( * ) Notice: Subject to any disclaimer, the term of this patent is extended or adjusted under 35 U.S.C. 154(b) by 471 days.

(21) Appl. No.: 10/917,463

(22) Filed: Aug. 13, 2004

(65) Prior Publication Data
US 2005/0043561 A1    Feb. 24, 2005

(30) Foreign Application Priority Data
Aug. 22, 2003 (DE) ................ 103 38 508

(51) Int. Cl.
*C07C 249/00* (2006.01)
*C07C 251/00* (2006.01)
*C07C 257/00* (2006.01)
*C07C 263/00* (2006.01)
*C07C 265/00* (2006.01)
*C07C 267/00* (2006.01)
*C07C 291/00* (2006.01)

(52) U.S. Cl. .................................... 560/330
(58) Field of Classification Search ................ 560/330
See application file for complete search history.

(56) References Cited

U.S. PATENT DOCUMENTS

| | | | |
|---|---|---|---|
| 2,692,275 A | 10/1954 | Bortnick et al. | |
| 3,919,279 A | 11/1975 | Rosenthal et al. | |
| 4,081,472 A | 3/1978 | Tsumura et al. | |
| 4,268,683 A | 5/1981 | Gurgiolo | |
| 4,386,033 A | 5/1983 | Koenig et al. | |
| 4,388,246 A | 6/1983 | Sundermann et al. | |
| 4,530,796 A | 7/1985 | Mattner et al. | |
| 4,596,678 A | 6/1986 | Merger et al. | |
| 4,596,679 A | 6/1986 | Hellbach et al. | |
| 4,692,550 A | 9/1987 | Engbert et al. | |
| 4,713,476 A | 12/1987 | Merger et al. | |
| 4,851,565 A | 7/1989 | Merger et al. | |
| 5,087,739 A | 2/1992 | Bohmholdt et al. | |
| 5,360,931 A | 11/1994 | Bohmholdt et al. | |
| 5,386,053 A * | 1/1995 | Otterbach et al. | 560/344 |
| 5,453,536 A | 9/1995 | Dai et al. | |
| 5,502,244 A | 3/1996 | Okawa et al. | |
| 5,616,784 A | 4/1997 | Schwarz et al. | |
| 5,646,328 A | 7/1997 | Deibele et al. | |
| 5,744,633 A | 4/1998 | Wilmes et al. | |
| 5,962,728 A | 10/1999 | Mason et al. | |
| 6,204,409 B1 | 3/2001 | Aso et al. | |
| 2005/0043561 A1 | 2/2005 | Kohlstruk et al. | |

FOREIGN PATENT DOCUMENTS

| | | |
|---|---|---|
| DE | 1 022 222 | 1/1958 |
| DE | 196 27 552 A1 | 1/1998 |
| DE | 101 27 273 | 12/2002 |
| EP | 0 355 443 A2 | 2/1990 |
| EP | 0 566 925 A2 | 10/1993 |
| EP | 0 568 782 A2 | 11/1993 |

OTHER PUBLICATIONS

U.S. Appl. No. 11/100,603, filed Apr. 7, 2005, Kohlstruk et al.
U.S. Appl. No. 11/101,428, filed Apr. 8, 2005, Kohlstruk et al.
U.S. Appl. No. 11/185,776, filed Jul. 21, 2005, Kohlstruk et al.
U.S. Appl. No. 10/917,463, filed Aug. 13, 2004, Kohlstruk et al.
U.S. Appl. No. 10/922,910, filed Aug. 23, 2004, Kohlstruk et al.
U.S. Appl. No. 10/921,934, filed Aug. 20, 2004, Kohlstruk et al.

* cited by examiner

*Primary Examiner*—Yvonne Eyler
*Assistant Examiner*—Kellette Gale
(74) *Attorney, Agent, or Firm*—Oblon, Spivak, McClelland, Maier & Neustadt, P.C.

(57) ABSTRACT

A process for continuous phosgene-free preparation of cycloaliphatic diisocyanates.

54 Claims, No Drawings

MULTISTAGE CONTINUOUS PREPARATION OF CYCLOALIPHATIC DIISOCYANATES

BACKGROUND OF THE INVENTION

1. Field of the Invention

The invention relates to a process for continuous phosgene-free preparation of cycloaliphatic diisocyanates.

2. Background of the Invention

The synthetic access route to isocyanates may be via a series of different routes. The variant for industrial scale preparation of isocyanates which is the oldest and still predominates today is what is known as the phosgene route. This process is based on the reaction of amines with phosgene. A disadvantage of the phosgene process is the use of phosgene which, as a consequence of its toxicity and corrosivity, places particularly high requirements on its handling on the industrial scale.

There are several processes which avoid the use of phosgene for preparing isocyanates on the industrial scale. The term phosgene-free process is frequently used in connection with the conversion of amines to isocyanates using alternative carbonylating agents, for example urea or dialkyl carbonate (EP 0 018 586, EP 0 355 443, U.S. Pat. No. 4,268,683, EP 0 990 644).

The urea route is based on the urea-mediated conversion of diamines to diisocyanates via a two-stage process. In the first step, a diamine is reacted with alcohol in the presence of urea or urea equivalents (for example alkyl carbonates, alkyl carbamates) to give a diurethane which typically passes through an intermediate purification stage and is then thermally cleaved in the second step to diisocyanate and alcohol (EP 0 355 443, U.S. Pat. No. 4,713,476, U.S. Pat. No. 5,386,053). Alternatively, the actual urethane formation may also be preceded by the separate preparation of a diurea by selectively reacting the diamine with urea (EP 0 568 782). Also conceivable is a two-stage sequence consisting of partial reaction of urea with alcohol in the first and subsequent metering in and urethanization of the diamine in the second step (EP 0 657 420).

The thermal cleavage of urethanes to the corresponding isocyanates and alcohols has been known for some time and can be carried out either in the gas phase at high temperatures or at relatively low temperatures in the liquid phase. However, a problem in both procedures is that the thermal stress inevitably also causes undesired side reactions to take place which firstly reduce the yield and secondly lead to the formation of resinifying by-products which considerably disrupt the course of an industrial process as a result of deposits and blockages in reactors and workup apparatus.

There has therefore been no shortage of suggestions of chemical and process technology measures to achieve yield improvements and limit the undesired by-product formation. For instance, a series of documents describes the use of catalysts which accelerate the cleavage reaction of the urethanes (DE 10 22 222, U.S. Pat. No. 3,919,279, DE 26 35 490). Indeed, it is entirely possible in the presence of suitable catalysts, which are a multitude of basic, acidic and also organometallic compounds, to increase the isocyanate yield in comparison to the uncatalyzed variant. However, the formation of undesired by-products can also not be prevented by the presence of a catalyst. The same applies to the additional use of inert solvents, as recommended in U.S. Pat. No. 3,919,279 and DE 26 35 490, in order to ensure uniform distribution of the heat supplied and of the catalyst in the reaction medium. However, the use of solvents boiling under reflux fundamentally has the consequence of a reduction in the space-time yield of isocyanates and is additionally hindered with the disadvantage of additional high energy demands.

Examples which are cited in EP 0 054 817 for thermal catalyzed cleavage of monourethanes describe the partial discharge of the reaction mixture to remove resinifying by-products formed in the course of the urethane cleavage. This procedure serves to prevent deposits and blockages in reactors and workup units. There are no indications which point to a yield-increasing utilization of the partial discharge. EP 0 061 013 describes a similar approach to a solution, in which the thermolysis is in this case carried out in the presence of solvents whose purpose is apparently to better absorb the involatile by-products. Here also, the partial discharge is not utilized for the purposes of yield optimization.

EP 0 355 443 discloses that a yield increase can be achieved when the higher molecular weight by-products which can and cannot be utilized and are formed in the cleavage reactor during the cleavage of diurethanes, to ensure a disruption-free and selective reaction, are discharged substantially continuously out of the reactor and subsequently converted for the most part in the presence of alcohol and then recycled into the diurethane preparation. The procedure described is associated with high energy demands, since nonutilizable by-products are removed from the effluent of the diurethane preparation by distillation, and all of the diurethane has to be evaporated. In contrast to EP 0 355 443, the urethanization effluent in the process of EP 0 566 925 is divided into two substreams of which only one is freed by distillation of its high-boiling, nonutilizable by-products, before the combined diurethane streams are fed to the deblocking reaction in the cleavage reactor. In addition, the continuous cleavage reactor discharge in EP 0 566 925 is recycled directly, i.e. without a reurethanization step, into the diurethane synthesis.

However, it has been found that the processes of EP 0 355 443 and EP 0 566 925, when cycloaliphatic diamines are used, are affected by a distinctly recognizable decrease in selectivity when the continuous process is maintained over a period of several hours.

SUMMARY OF THE INVENTION

It is therefore an object of the present invention to provide a process for continuously preparing cycloaliphatic diisocyanates which affords good yields and is not burdened with the disadvantage described of a distinctly recognizable decrease in selectivity in the course of operation for several hours.

This object is achieved by the finding of a continuous process by which the diurethanes, after their synthesis by reacting cycloaliphatic diamines with alcohol and a suitable carboxylating agent such as urea and/or urea equivalents, are freed of low, medium and high boilers, the cycloaliphatic diurethane purified in this way is thermally cleaved to release the desired cycloaliphatic diisocyanate, a portion of the dissociation residue of the dissociation apparatus is continuously discharged and reurethanized with alcohol, and the reurethanized stream is recycled directly into the low boiler removal.

The invention provides a multistage process for continuously preparing cycloaliphatic diisocyanates, by reacting cycloaliphatic diamines with carbonic acid derivatives and alcohols to give cycloaliphatic diurethanes and subsequently thermally cleaving the diurethanes to give cycloaliphatic diisocyanates, which comprises freeing the diurethanes, after their synthesis by reacting cycloaliphatic diamines with alcohol and urea and/or urea derivatives, of low, middle and high boilers, thermally cleaving the cycloaliphatic diurethane purified in this way to release the desired cycloaliphatic diisocyanate, continuously discharging a portion of the cleavage residue from the cleavage apparatus and reurethanizing it with alcohol and recycling the reurethanization product directly into the low-boiler removal.

The invention also provides a multistage process for continuously preparing cycloaliphatic diisocyanates of the formula (I):

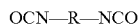

OCN—R—NCO where R is a bivalent cycloaliphatic hydrocarbon radical having from 4 to 18, preferably from 5 to 15, carbon atoms, with the proviso that the two isocyanate groups are bonded directly to a hydrocarbon cycle and at least 3 carbon atoms are disposed between them, by reacting cycloaliphatic diamines with urea and/or urea derivatives and alcohols to give cycloaliphatic diurethanes and thermally cleaving them, wherein a) cycloaliphatic diamines of the formula (II):

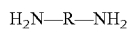

$H_2N$—R—$NH_2$ where R is a bivalent cycloaliphatic hydrocarbon radical having from 4 to 18, preferably from 5 to 15, carbon atoms, with the proviso that the two nitrogen atoms are bonded directly to one hydrocarbon cycle and at least 3 carbon atoms are disposed between them, are reacted with urea and/or urea derivatives and alcohols of the formula (III):

$R^1$—OH where $R^1$ is a radical as remains after removal of the hydroxyl group from a primary or secondary (cyclo) aliphatic alcohol having from 3 to 8 carbon atoms, in the absence or presence of dialkyl carbonates, alkyl carbamates or mixtures of dialkyl carbonates and carbamic esters and in the absence or presence of catalysts to give cycloaliphatic diurethanes, and the ammonia formed is simultaneously removed;

b) the alcohol, the dialkyl carbonates and/or alkyl carbamates are removed from the resulting reaction mixture, and the alcohol and optionally the dialkyl carbonates and/or alkyl carbamates are recycled into the reaction stage a);

c) the material stream substantially comprising diurethanes from stage b) is separated by distillation into a material-of-value stream and a by-product stream which is discharged, d) the reaction mixture comprising the diurethanes purified by steps b) and c) is continuously and thermally cleaved in the presence of a catalyst and without solvent, at temperatures of from 180 to 280° C., preferably from 200 to 260° C., and under a pressure of from 0.1 to 200 mbar, preferably from 0.2 to 100 mbar, in such a way that a portion of the reaction mixture of from 10 to 60% by weight based on the feed, preferably from 15 to 45% by weight based on the feed, is constantly discharged;

e) the cleavage products are separated by rectification into crude cycloaliphatic diisocyanate and alcohol;

f) the crude cycloaliphatic diisocyanate is purified by distillation and the pure product fraction is isolated;

g) the bottoms discharge from d) is reacted with the alcohol from e) in the presence or absence of catalysts within from 1 to 150 min, preferably from 3 to 60 min, at temperatures of from 20 to 200° C., preferably from 50 to 170° C., and a pressure of from 0.5 to 20 bar, preferably from 1 to 15 bar, at a molar ratio of NCO groups to OH groups of up to 1:100, preferably 1:20 and more preferably 1:10;

h) a portion of the bottoms fraction of the purification by distillation f) is continuously discharged and conducted into the cleavage reaction d), but preferably into the urethanization stage g);

i) the top fraction obtained in the purification by distillation of the cycloaliphatic diisocyanate is likewise recycled into the urethanization stage g) or discarded;

j) the reurethanized stream from g) is recycled into stage b), or k) the reurethanized stream from g) is recycled into the reaction stage a), under the condition that g) is carried out in the presence of catalysts which are preferably selected from the halides of Fe(III) and/or Cu(I).

Thus, the present invention is directed to a multistage process for continuously preparing cycloaliphatic diisocyanates, comprising:

reacting a cycloaliphatic diamine with a carbonic acid derivative and an alcohol to produce a cycloaliphatic diurethane, serparating the cycloaliphatic diurethane from low, middle and high boilers, and then thermally cleaving the cycloaliphatic diurethane to produce a cycloaliphatic diisocyanate, and continuously discharging a portion of the cleavage residue and reurethanizing said portion with an alcohol, and recycling the reurethanization product directly into the low-boiler separation.

The present invention is also directed to a multistage process for continuously preparing cycloaliphatic diisocyanates of the formula (I):

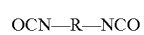

OCN—R—NCO wherein R is a bivalent cycloaliphatic hydrocarbon radical having from 4 to 18, preferably from 5 to 15, carbon atoms, with the proviso that the two isocyanate groups are bonded directly to a hydrocarbon cycle and at least 3 carbon atoms are disposed between them, comprising:

(a) reacting a cycloaliphatic diamine of the formula (II):

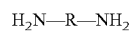

$H_2N$—R—$NH_2$ wherein R is a bivalent cycloaliphatic hydrocarbon radical having from 4 to 18 carbon atoms, with the proviso that the two nitrogen atoms are bonded directly to one hydrocarbon cycle and at least 3 carbon atoms are disposed between them, with urea and/or a urea derivatives and an alcohol of the formula (III):

$R^1$—OH wherein $R^1$ is a radical as remains after removal of the hydroxyl group from a primary or secondary (cyclo) aliphatic alcohol having from 3 to 8 carbon atoms, in the absence or presence of a dialkyl carbonate, alkyl carbamate or mixture of dialkyl carbonate and carbamic ester and in the absence or presence of a catalyst, to produce a cycloaliphatic diurethane and ammonia, with the simultaneous removal of the ammonia;

(b) removing the alcohol, the dialkyl carbonate and/or alkyl carbamate from the resulting reaction mixture obtained in (a), and recycling the alcohol and optionally the dialkyl carbonate and/or alkyl carbamate to (a);

(c) distilling the material stream from (b) to produce a material-of-value stream and a by-product stream which is discharged;
(d) continuously and thermally cleaving the material-of-value stream from (c) in the presence of a catalyst and without solvent, at a temperature of from 180 to 280° C., and under a pressure of from 0.1 to 200 mbar, in such a way that a portion of the reaction mixture of from 10 to 60% by weight based on the feed, is constantly discharged;
(e) rectifying the cleavage products from (d) into a crude cycloaliphatic diisocyanate and alcohol;
(f) distilling the crude cycloaliphatic diisocyanate from (e) to produce a pure product fraction, a top fraction, and a bottoms fraction, and isolating the pure product fraction;
(g) reacting the discharge from (d) with the alcohol obtained from (e) in the presence or absence of a catalyst within from 1 to 150 min, at a temperature of from 20 to 200° C., and a pressure of from 0.5 to 20 bar, at a molar ratio of NCO groups to OH groups of up to 1:100, to produce a reurethanized stream;
(h) continuously discharging a portion of the bottoms fraction produced in (f) and conducting said portion into (d) or (g);
(i) recycling the top fraction produced in (f) to (g) or discarding said top fraction;
(j) recycling the reurethanized stream from (g) to (b) or
(k) recycling the reurethanized stream from (g) to (a), wherein (g) is carried out in the presence of a catalyst.

In the process according to the invention, cycloaliphatic diisocyanates can be prepared continuously, without any problem and with very good selectivity. Especially advantageous in the multistage process according to the invention is the fact that it proceeds with high selectivity and without disruption over a long period even when cycloaliphatic diamines of the formula (II) are used as starting material for the continuous diisocyanate synthesis.

DETAILED DESCREPTION OF THE INVENTION a) To prepare the monomeric cycloaliphatic diurethanes in reaction stage a), the cycloaliphatic diamines of the formula (II) are reacted with urea and/or urea derivatives which are suitable as carboxylating agents and an alcohol of the formula (III), in some cases also mixtures of such alcohols, in a molar ratio of from 1:2.01:4.0 to 1:2.2:10, preferably from 1:2.02:6 to 1:2.12:9, optionally but not preferably in the presence of dialkyl carbonates, alkyl carbamates or mixtures of dialkyl carbonates and carbamic esters, in an amount of in each case 1-10 mol % based on the diamine, in the absence or presence of catalysts, at reaction temperatures of from 140-270° C., preferably 160-250° C., and under a pressure which, depending on the alcohol used, is between 2-80 bar, preferably 7-15 bar, within from 2 to 20 hours, preferably 4-9 hours. The conversion may be effected in a continuous stirred tank battery, but preferably in a pressure distillation reactor.

To increase the reaction rate, the diurethanes may be prepared in the presence of catalysts. Suitable catalysts are inorganic or organic compounds which contain one or more, preferably a cation of, metals or groups IA, IB, IIA, IIB, IIIA, IIIB, IVA, IVB, VA, VB, VIB, VIIB and VIIIB of the Periodic Table, defined in accordance with Handbook of Chemistry and Physics 14$^{th}$ Edition, published by Chemical Rubber Publishing Co. 2310 Superior Ave. N.E. Cleveland, Ohio, for example halides such as chlorides and bromides, sulfates, phosphates, nitrates, borates, alkoxides, phenoxides, sulfonates, oxides, oxide hydrates, hydroxides, carboxylates, chelates, carbonates and thio- or dithiocarbamates. Examples include the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt and nickel. Examples of typical catalysts include the following compounds: lithium ethoxide, lithium butoxide, sodium methoxide, potassium tert-butoxide, magnesium ethoxide, calcium methoxide, tin(II) chloride, tin(IV) chloride, lead acetate, aluminum trichloride, bismuth trichloride, copper(II) acetate, copper(II) chloride, zinc chloride, zinc octoate, titanium tetrabutoxide, vanadium trichloride, vanadium acetylacetonate, manganese(II) acetate, iron(II) acetate, iron (III) acetate, iron oxalate, cobalt chloride, cobalt naphthenate, nickel chloride, nickel naphthenate and mixtures thereof. The catalysts may optionally also be used in the form of their hydrates or ammoniates.

Starting compounds for the process according to the invention are cycloaliphatic diamines of the formula (II) which has already been mentioned above, alcohols of the formula (III) which has already been mentioned above, and also urea or urea derivatives which are suitable as carboxylating agents, in the absence or presence of dialkyl carbonates, alkyl carbamates or mixtures of dialkyl carbonates and alkyl carbamates. Suitable diamines of the formula (II) are, for example, 1,4-diaminocyclohexane, 4,4'-dicyclohexylmethanediamine, 2,4-dicyclohexylmethanediamine, 2,2'-dicyclohexylmethanediamine and isomeric cycloaliphatic diamines, and also perhydrogenated diphenylmethanediamine. As a result of the preparation, diphenylmethanediamine (MDA) occurs as an isomer mixture of 4,4'-, 2,4- and 2,2'-MDA (see, for example, DE 101 27 273). Perhydrogenated diphenylmethanediamine is obtained by fully hydrogenating MDA and is accordingly a mixture of isomeric dicyclohexylmethanediamines ($H_{12}$MDA), i.e. 4,4'-, 2,4- and 2,2'-$H_{12}$MDA. The diamines of the formula (II) used are preferably 4,4'-dicyclohexylmethanediamine, 2,4-dicyclohexylmethanediamine and 2,2'-dicyclohexylmethanediamine, and also any mixtures of at least two of these isomers. It will be appreciated that diamines may also be used which deviate from the formula (II). Examples include 1,3- and 1,4-diaminomethylcyclohexane, 1,6-hexanediamine, 2,2,4- or 2,4,4-trimethyl-1,6-hexanamine and 3-aminomethyl-3,5,5-trimethylcyclohexylamine. However, preference is not given to using amines which deviate from the formula (II).

Suitable alcohols of the formula (III) are any aliphatic or cycloaliphatic alcohols which have a boiling point below 190° C. under atmospheric pressure. Examples include C1-C6-alkanols, for example methanol, ethanol, 1-propanol, 1-butanol, 2-butanol, 1-hexanol or cyclohexanol. The alcohol used is preferably 1-butanol.

In the course of the conversion of the reaction mixture, ammonia is released, whose removal from the reaction equilibrium has been found to be advantageous. When ammonia is discharged from the reactor, care has to be taken that the wall temperatures of the reactor and of the discharge tube are above 60° C., so that deposition of ammonium carbamate, which is formed in minimal amounts from ammonia and carbon dioxide by decomposition of urea, can be prevented. It has been found to be useful, for example, to carry out the reaction in a pressure distillation reactor, in which case the reaction mixture is conducted in countercurrent to alcohol vapors introduced in the bottom and in this way such intensive mixing of the liquid proceeds on the trays that they each virtually correspond to a battery stage. The vaporous mixture of alcohol and ammonia which is withdrawn at the top may, preferably under the pressure of the pressure distillation reactor and without condensing it beforehand, be conducted into a distillation column, in order, from the ammonia, to obtain free alcohol which is recycled into the bottom of the pressure distillation reactor and of the column. In order to prevent fouling of the reflux condenser with ammonium carbamate, an appropriate proportion of alcohol is permitted therein to set the temperature at the top to at least 60° C.

b) The excess alcohol, the dialkyl carbonates, if they have been formed or are present in the reaction mixture, or alkyl carbamates or mixtures of at least two of these components are advantageously removed in two stages. At the first stage, the reaction mixture is decompressed from the pressure level of reaction stage a) to a pressure of from 1 to 500 mbar, preferably from 2 to 150 mbar, and in this way separated into gaseous vapors which contain the predominant amount of alcohol and also any dialkyl carbonates and/or alkyl carbamates, and into a liquid effluent. In the second stage, the liquid effluent is freed of any remaining residual alcohol and also medium boilers such as dialkyl carbonates and/or alkyl carbamates by thin-film evaporation at from 180 to 250° C., preferably from 200 to 230° C., and a pressure of from 0.1 to 20 mbar, preferably from 1 to 10 mbar, so that the residue consists substantially of the monomeric diurethane, and in some cases high-boiling oligomers.

The vapors may, preferably after distillative purification, optionally be recycled into reaction stage a).

c) The liquid stream which contains the monomeric diurethanes and any high-boiling oligomers and is obtained after the removal of the vapors from step b) is separated, preferably with the aid of a thin-film or short-path evaporator, at a temperature of from 180 to 260° C., preferably from 200 to 240° C., and under a pressure of from 0.01 to 10 mbar, preferably from 0.02 to 5 mbar, by distillation into a material-of-value stream which contains the monomeric diurethanes and the lower-boiling by-products and a non-distillable by-product stream which is discharged from the preparative process and is typically discarded as a residue whose material cannot be utilized.

Optionally, the stream from stage b) which contains any high-boiling oligomers, before its above-described distillative purification, may also be divided into two substreams of which one is fed directly to the cleavage reaction (stage d)) and the other initially passes through the high boiler removal already described.

d) The material-of-value stream which contains the monomeric diurethanes and the lower-boiling by-products is partly and continuously thermally cleaved in a suitable apparatus, without solvents in the liquid phase in the presence of catalysts at temperatures of from 180 to 280° C., preferably from 200 to 260° C., and under a pressure of from 0.1 to 200 mbar, preferably from 0.2 to 100 mbar. The conversion of diurethane to diisocyanate in the apparatus for thermal cleavage may, depending on the polyurethane used, be selected substantially freely and is typically within the range of from 10 to 95% by weight, preferably from 35 to 85% by weight of the diurethane feed. The uncleaved proportion of the reaction mixture which contains unconverted diurethanes, high-boiling by-products and other reutilizable and nonutilizable by-products is continuously discharged. The amount of the discharge is governed, inter alia, by the desired conversion and the desired capacity of the cleavage reaction and can be easily determined experimentally. It is typically from 10 to 60% by weight, preferably from 15 to 45% by weight, based on the feed.

Useful catalysts for chemically cleaving the diurethanes are, for example, the aforementioned inorganic and organic compounds which catalyze urethane formation. Preference is given to using chlorides of zinc or tin, and also zinc oxides, manganese oxides, iron oxides or cobalt oxides, in which case the catalyst is metered into the material-of-value stream from the purification step c), before it is fed into the cleavage, as a from 0.01 to 25% by weight, preferably from 0.05 to 10% by weight, solution or suspension, into the alcohol which is also used for urethane preparation, in an amount of from 5 to 400 ppm, preferably from 10 to 100 ppm.

Suitable cleavage apparatus is, for example, cylindrical cleavage reactors, for example tubular furnaces or preferably evaporators such as falling-film, thin-film or bulk evaporators, selected from Robert evaporators, Herbert evaporators, Caddle-type evaporators, Oskar evaporators and heating cartridge evaporators.

In principle, the main concern is to keep the average residence time of isocyanate groups, which are inevitably released when the alcohol is deblocked, in the cleavage zone very low and thus to limit undesired side reactions to a minimum.

Preference is given to carrying out the cleavage in a combined cleavage and rectification column, which is equipped for the energy supply in the bottom with a falling-film evaporator, in the lower third with a unit for additional energy input or for energy recovery, in the upper third with a unit to remove crude diisocyanate and at the top with a condenser for the reflux and the removal of pure alcohol.

e) The cleavage products which are formed in the thermal cleavage in stage d) and are composed in particular of alcohol, diisocyanate and partially cleaved diurethanes are separated by rectification at from 95 to 260° C., preferably from 110 to 245° C., and a pressure of from 0.5 to 250 mbar, preferably from 1 to 100 mbar, into alcohol and into a crude fraction, consisting of cycloaliphatic diisocyanate, partially cleaved cycloaliphatic diisocyanate and in some cases small amounts of cycloaliphatic diurethane. This separation may be carried out, for example, in the cleavage column of the abovementioned combined cleavage and rectification column (stage d)).

f) The crude fraction which is preferably obtained by rectification in stage e), consisting of cycloaliphatic diisocyanate, partially cleaved cycloaliphatic diurethane and in some cases small fractions of cycloaliphatic diurethane, is purified by distillation at a temperature of from 95 to 260° C., preferably from 110 to 245° C., and under a pressure of from 0.5 to 150 mbar, preferably from 1 to 75 mbar, and the resulting fractions are recycled to stage g) or isolated as a pure product.

g) The bottoms discharge from the cleavage stage d) is combined with the alcohol from the rectification stage e), in a molar ratio of NCO groups to OH groups of up to 1:100, preferably 1:20 and more preferably 1:10, and the reaction mixture is converted, in the presence or absence of catalysts, within from 1 to 150 min, preferably from 3 to 60 min, at temperatures of from 20 to 200° C., preferably from 50 to 170° C., and a pressure of from 0.5 to 20 bar, preferably from 1 to 15 bar. The reaction may be carried out in a continuous tank battery or in a tubular reactor. Useful catalysts are in principle all catalysts which support the NCO/OH reaction. Examples include tin octoate, dibutyltin laurate, tin dichloride, zinc dichloride and triethylamine.

h) A portion of the bottoms fraction of the purifying distillation f) is continuously discharged and optionally recycled into the cleavage stage d) or into the urethanization stage g). Preference is given to recycling into the urethanization stage. The amount of the discharge is from 0.1 to 50% by weight, preferably from 0.2 to 25% by weight, of the feed of crude diisocyanate into the purifying distillation stage.

i) The top fraction of the purifying distillation stage f) may be discarded or preferably recycled into the urethanization stage g). The amount of top fraction removed per unit time is from 0.1 to 3% by weight, preferably from 0.3 to 1% by weight, of the feed of crude diisocyanate into the purifying distillation.

j) The stream from the urethanization stage f) is recycled into the low and medium boiler removal b).

k) Alternatively to the recycling described under j), the stream from the urethanization stage g) may also be recycled into the diurethane preparation a), as long as the urethanization was carried out in the presence of specific Lewis acid catalysts. In this context, specific catalysts refer to halides of Fe(III) or Cu(I) or mixtures thereof. Examples include Fe(III) chloride, Fe(III) bromide, Cu(I) chloride and Cu(I) bromide. The use of these specific catalysts does not fundamentally rule out the simultaneous use of other catalysts which serve to accelerate the urethanization. Preference is given to using the specific catalysts, i.e. the halides of Fe(III) or Cu(I) or mixtures thereof, without additionally using further catalysts.

The multistage process according to the invention for continuously preparing cycloaliphatic diisocyanates with recycling and discharge of the by-products allows, for distillable cycloaliphatic polyisocyanates, preferably diisocyanates, a reaction which proceeds without disruption and with high selectivity to be ensured over a long period of time. The process according to the invention is suitable in particular for preparing cycloaliphatic diisocyanates having from 4 to 18, preferably from 5 to 15, carbon atoms, such as 1,4-diisocyanatocyclohexane, 4,4'-dicyclohexylmethane diisocyanate (4,4'-$H_{12}$MDI), 2,2'-dicyclohexylmethane diisocyanate (2,2'-$H_{12}$MDI), 2,4'-dicyclohexylmethane diisocyanate (2,4'-$H_{12}$MDI) or else mixtures of the aforementioned isomeric dicyclohexylmethane diisocyanates ($H_{12}$MDI), as are obtained, for example, by the nature of the conversion of perhydrogenated MDA to $H_{12}$MDI.

The cycloaliphatic diisocyanates prepared are excellently suited to preparing polymers containing urethane, isocyanurate, amide and/or urea groups by the polyisocyanate polyaddition process. They additionally find use for preparing polyisocyanate mixtures modified with urethane, biuret and/or isocyanurate groups. Such polyisocyanate mixtures of cycloaliphatic diisocyanates are used in particular for preparing high-value, light-resistant polyurethane coatings.

EXAMPLES

The following Examples are intended to illustrate the invention. The invention is not limited by these Examples.

The amounts reported are average values which were obtained after operating the particular circulation experiment in the steady state for 10-12 hours.

Example 1

Preparation According to the Invention of Dicyclohexylmethane Diisocyanate ($H_{12}$MDI) from Perhydrogenated Diphenylmethanediamine ($H_{12}$MDA) and Urea in the Presence of n-butanol—Recycling of the Diurethanized Material to the Flash Stage Every hour, the uppermost tray of a pressure distillation reactor was charged with 255.3 g of $H_{12}$MDA, 149.3 g of urea and 545 g of n-butanol, and the reaction mixture was boiled at 220° C. and an average residence time of 8.5 hours while continuously removing the ammonia released at 11-14 bar. The reactor effluent, together with the stream from the reurethanization, was subsequently freed of excess alcohol, low boilers and medium boilers in the flash vessel at 55 mbar with subsequent thin-film evaporation at 220° C. and 2 mbar, and fed to high boiler removal by short-path evaporation at 0.08 mbar. The remaining 605.9 g/h of bis(4-butoxycarbonylaminocyclohexyl)methane ($H_{12}$MDU) were conducted as a melt (140° C.) into the circulation of the falling-film evaporator of the cleavage and rectification column, and the deblocking reaction was carried out at a temperature of 236° C. and a bottom pressure of 10 mbar in the presence of a steady-state concentration of tin dichloride of 16 ppm. The cleavage gases, $H_{12}$MDI and butanol, were condensed out in two condensers connected in series at 85° C. and −25° C. The resulting about 97% crude $H_{12}$MDI was fed to a purifying distillation where 270.33 g/h of $H_{12}$MDI having a purity of >99.5% were obtained, which corresponds to a selectivity of 85%. 177.2 g/h of butanol were obtained as the top product of the cleavage and rectification column. To maintain constant mass within the cleavage and rectification column and avoid fouling and blockages of the cleavage apparatus, 147.6 g/h were continuously discharged from the circuit and combined together with 24.0 g/h of material separated from the bottoms of the $H_{12}$MDI purifying distillation, and also the top product from the cleavage and rectification column, and reurethanized. The reurethanized material was fed to the flash vessel together with the reactor effluent of the diurethane preparation.

Example 2

Preparation According to the Invention of Dicyclohexylmethane Diisocyanate ($H_{12}$MDI) from Perhydrogenated Diphenylmethanediamine ($H_{12}$MDA) and Urea in the Presence of n-butanol—Reurethanization in the Presence of CuCl and Recycling of the Reurethanized Material into the Diurethane Synthesis Every hour, the uppermost tray of a pressure distillation reactor was charged with 255.3 g of $H_{12}$MDA, 149.3 g of urea and 545 g of n-butanol and the stream from the catalytic reurethanization, and the reaction mixture was boiled while continuously removing the ammonia released at 11-14 bar, 220° C. and an average residence time of 8.5 hours. The reactor effluent, together with the stream from the reurethanization, was freed at 220° C. and 2 mbar of excess alcohol, low and medium boilers in the flash vessel at 55 mbar with subsequent thin-film evaporation and the high boiler removal was carried out by short-path evaporation at 0.08 mbar. The remaining 601.1 g/h of bis(4-butoxycarbonylaminocyclohexyl)methane ($H_{12}$MDU) were conducted as a melt (140° C.) into the circulation of the falling-film evaporator of the cleavage and rectification column, where the deblocking reaction was carried out at a temperature of 236° C. and a bottom pressure of 10 mbar in the presence of a steady-state concentration of tin dichloride of 16 ppm. The cleavage gases, $H_{12}$MDI and butanol, were condensed out in two condensers connected in series at 85 and −25° C. The resulting about 97% crude $H_{12}$MDI was fed to a purifying distillation to obtain 268.2 g/h of $H_{12}MDI$ having a purity of >99.5%, which corresponds to a selectivity of 84%. 175.9 g/h of butanol were obtained as the top product of the cleavage and rectification column. To maintain constant mass within the cleavage and rectification column and prevent fouling and blockages of the cleavage apparatus, 145.6 g/h were continuously discharged from the circuit and combined together with 23.9 g/h of material separated from the bottoms of the $H_{12}MDI$ purifying distillation, and also the top product from the cleavage and rectification column, and reurethanized in the presence of 100 ppm of CuCl. The reurethanized material was fed to the diurethane preparation in the pressure distillation reactor.

Comparative Example 1

Preparation of Dicyclohexylmethane Diisocyanate ($H_{12}MDI$) from Perhydrogenated Diphenylmethanediamine ($H_{12}MDA$) and Urea in the Presence of n-butanol—Reurethanization and Recycling of the Reurethanized Material into the Diurethane Synthesis Every hour, the uppermost tray of a pressure distillation reactor was charged with 255.3 g of $H_{12}MDA$, 149.3 g of urea and 545 g of n-butanol, and also with the stream from the reurethanization, and the reaction mixture was boiled while continuously removing the ammonia released at 11-14 bar, 220° C. and an average residence time of 8.5 h. The reactor effluent was freed of excess alcohol, low and medium boilers in a flash vessel at 55 mbar and subsequent thin-film evaporation at 220° C. and 2 mbar, and fed to the high boiler removal by short-path evaporation at 0.08 mbar. The remaining 575.1 g/h of bis(4-butoxycarbonylaminocyclohexyl)methane ($H_{12}MDU$) were conducted as a melt (140° C.) into the circulation of the falling-film evaporator of the cleavage and rectification column, and the deblocking reaction was carried out at a temperature of 236° C. and a bottom pressure of 10 mbar in the presence of a steady-state concentration of tin dichloride of 16 ppm. The cleavage gases, $H_{12}MDI$ and butanol, were condensed out at 85° C. and −25° C. in two condensers connected in series. The about 97% crude $H_{12}MDI$ obtained was fed to a purifying distillation to obtain 252.9 g/h of $H_{12}MDI$ having a purity of >99.5%, which corresponds to a selectivity of 79%. 163.5 g/h of butanol were obtained as the top product of the cleavage and rectification column. To maintain constant mass within the cleavage and rectification column, and prevent fouling and blockages of the cleavage apparatus, 139.9 g/h were discharged from the circulation circuit and combined with 22.6 g/h of material separated from the bottoms of the $H_{12}MDI$ purifying distillation, and also with the top product from the cleavage and rectification column, and reurethanized. The reurethanized material was fed to diurethane preparation in the pressure distillation reactor.

The starting selectivity of the circuit experiment was approx. 84%. However, it decreased continuously in the course of the experiment (12 h) and at the end fell below 75%.

Comparative Example 2

Preparation of Dicyclohexylmethane Diisocyanate ($H_{12}MDI$) from Perhydrogenated Diphenylmethanediamine ($H_{12}MDA$) and Urea in the Presence of n-butanol—Direct Recycling of the Cleavage Discharge into the Diurethane Synthesis Every hour, the uppermost tray of a pressure distillation reactor was charged with 255.3 g of $H_{12}MDA$, 149.3 g of urea and 545 g of n-butanol and also with the stream from the cleavage reactor discharge and the top product of the cleavage and rectification column (butanol), and the reaction mixture was boiled while continuously removing the ammonia released at 11-14 bar, 220° C. and an average residence time of 8.5 h. The reactor effluent was freed of excess alcohol, low and medium boilers in a flash vessel at 55 mbar and subsequent thin-film evaporation at 220° C. and 2 mbar, and fed to the high boiler removal by short-path evaporation at 0.08 mbar. The remaining 571.8 g/h of bis(4-butoxycarbonylaminocyclohexyl)methane ($H_{12}MDU$) were conducted as a melt (140° C.) into the circulation of the falling-film evaporator of the cleavage and rectification column, and the deblocking reaction was carried out at a temperature of 236° C. and a bottom pressure of 10 mbar in the presence of a steady-state concentration of tin dichloride of 16 ppm. The cleavage gases, $H_{12}MDI$ and butanol, were condensed out in two condensers connected in series at 85° C. and −25° C. The about 97% crude $H_{12}MDI$ obtained was fed to a purifying distillation to obtain 249.8 g/h of $H_{12}MDI$ having a purity of >99.5%, which corresponds to a selectivity of 78%. 160.6 g/h of butanol were obtained as the top product of the cleavage and rectification column. To maintain constant mass within the cleavage and rectification column, and prevent fouling and blockages of the cleavage apparatus, 137.5 g/h were discharged from the circulation circuit and fed without reurethanization to the diurethane preparation in the pressure distillation reactor. 22.8 g/h of material separated from the bottoms of the $H_{12}MDI$ purifying distillation were recycled into the circulation of the cleavage apparatus.

The starting selectivity of the circulation experiment was approx. 83%. However, it decreased continuously in the course of the experiment (12 h) and fell at the end to below 75%.

This application is based on German application No. 103 38 508.8, filed on Aug. 22, 2003, and incorporated herein by reference.

What is claimed is:

1. A multistage process for continuously preparing cycloaliphatic diisocyanates, comprising:
   reacting a cycloaliphatic diamine with a carbonic acid derivative and an alcohol to produce a cycloaliphatic diurethane,
   serparating the cycloaliphatic diurethane from low, middle and high boilers, and then
   thermally cleaving the cycloaliphatic diurethane to produce a cycloaliphatic diisocyanate, and
   continuously discharging a portion of the cleavage residue and reurethanizing said portion with an alcohol, and recycling the reurethanization product directly into the low-boiler separation.

2. A multistage process for continuously preparing cycloaliphatic diisocyanates of the formula (I):

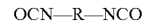
OCN—R—NCO wherein R is a bivalent cycloaliphatic hydrocarbon radical having from 4 to 18, preferably from 5 to 15, carbon atoms, with the proviso that the two isocyanate groups are bonded directly to a hydrocarbon cycle and at least 3 carbon atoms are disposed between them,
comprising:
   (a) reacting a cycloaliphatic diamine of the formula (II):

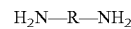
$H_2N$—R—$NH_2$ wherein R is a bivalent cycloaliphatic hydrocarbon radical having from 4 to 18 carbon atoms, with the proviso that the two nitrogen atoms are bonded directly to one hydrocarbon cycle and at least 3 carbon atoms are disposed between them, with urea and/or a urea derivatives and an alcohol of the formula (III):

wherein R¹ is a radical as remains after removal of the hydroxyl group from a primary or secondary (cyclo) aliphatic alcohol having from 3 to 8 carbon atoms, in the absence or presence of a dialkyl carbonate, alkyl carbamate or mixture of dialkyl carbonate and carbamic ester and in the absence or presence of a catalyst, to produce a cycloaliphatic diurethane and ammonia, with the simultaneous removal of the ammonia;

(b) removing the alcohol, the dialkyl carbonate and/or alkyl carbamate from the resulting reaction mixture obtained in (a), and recycling the alcohol and optionally the dialkyl carbonate and/or alkyl carbamate to (a);

(c) distilling the material stream from (b) to produce a material-of-value stream and a by-product stream which is discharged;

(d) continuously and thermally cleaving the material-of-value stream from (c) in the presence of a catalyst and without solvent, at a temperature of from 180 to 280° C., and under a pressure of from 0.1 to 200 mbar, in such a way that a portion of the reaction mixture of from 10 to 60% by weight based on the feed, is constantly discharged;

(e) rectifying the cleavage products from (d) into a crude cycloaliphatic diisocyanate and alcohol;

(f) distilling the crude cycloaliphatic diisocyanate from (e) to produce a pure product fraction, a top fraction, and a bottoms fraction, and isolating the pure product fraction;

(g) reacting the discharge from (d) with the alcohol obtained from (e) in the presence or absence of a catalyst within from 1 to 150 min, at a temperature of from 20 to 200° C., and a pressure of from 0.5 to 20 bar, at a molar ratio of NCO groups to OH groups of up to 1:100, to produce a reurethanized stream;

(h) continuously discharging a portion of the bottoms fraction produced in (f) and conducting said portion into (d) or (g);

(i) recycling the top fraction produced in (f) to (g) or discarding said top fraction;

(j) recycling the reurethanized stream from (g) to (b) or (k) recycling the reurethanized stream from (g) to (a), wherein (g) is carried out in the presence of a catalyst.

3. The multistage process of claim 2, wherein (g) is carried out in the presence of a catalyst, and the catalyst is selected from the group consisting of the halides of Fe(III) and the halides of Cu(I).

4. The multistage process of claim 1, wherein the cycloaliphatic diamine is 4,4'-dicyclohexylmethanediamine, 2,4-dicyclohexylmethanediamine and 2,2'-dicyclohexylmethanediamine, or a mixture thereof.

5. The multistage process of claim 2, wherein the cycloaliphatic diamine is 4,4'-dicyclohexylmethanediamine, 2,4-dicyclohexylmethanediamine and 2,2'-dicyclohexylmethanediamine, or a mixture thereof.

6. The multistage process of claim 1, wherein the cycloaliphatic diamine is 4,4'-dicyclohexylmethanediamine and/or an isomeric cycloaliphatic diamine.

7. The multistage process of claim 2, wherein the cycloaliphatic diamine is 4,4'-dicyclohexylmethanediamine and/or an isomeric cycloaliphatic diamine.

8. The multistage process of claim 1, wherein the cycloaliphatic diamine is 1,4-diaminocyclohexane.

9. The multistage process of claim 2, wherein the cycloaliphatic diamine is 1,4-diaminocyclohexane.

10. The multistage process of claim 1, wherein said reacting is carried out continuously in a distillation reactor or in a stirred tank battery.

11. The multistage process of claim 2, wherein (a) is carried out continuously in a distillation reactor or in a stirred tank battery.

12. The multistage process of claim 1, wherein the reaction is effected at a molar ratio of diamine:alcohol of from 1:4.0 to 1:10.

13. The multistage process of claim 2, wherein the reaction in (a) is effected at a molar ratio of diamine:urea:alcohol of from 1:2.01:4.0 to 1:2.2:10.

14. The multistage process of claim 2, wherein the residence time of the reactants in (a) is from 2 to 20 hours, preferably from 4 to 9 hours.

15. The multistage process of claim 2, wherein (a) is carried out in a reactor at a temperature of from 140 to 270° C. and a pressure of from 2 to 80 bar.

16. The multistage process of claim 2, wherein (a) is carried out at a reaction temperature of from 160 to 250° C. and at a pressure of from 7 to 15 bar.

17. The multistage process of claim 2, wherein (a) is carried out in a pressure distillation reactor.

18. The multistage process of claim 2, wherein, in (a), the reactants are supplied continuously to the uppermost tray and the ammonia released is driven out by alcohol vapors which are introduced into the bottom of the distillation reactor.

19. The multistage process of claim 1, wherein the alcohol has from 1-6 carbon atoms.

20. The multistage process of claim 2, wherein the alcohol having from 1-6 carbon atoms.

21. The multistage process of claim 1, wherein the alcohol is butanol.

22. The multistage process of claim 2, wherein the alcohol is butanol.

23. The multistage process of claim 2, wherein the reaction in (a) is carried out in the presence of a catalyst.

24. The multistage process of claim 2, wherein (b) is carried out in two stages.

25. The multistage process of claim 24, wherein, in the first stage of (b), the reaction mixture is decompressed from the pressure level of the reaction in (a) to a pressure of from 1 to 500 mbar.

26. The multistage process of claim 24, wherein, in the second stage of (b), the liquid effluent is freed of any residual alcohol present and also middle boilers such as dialkyl carbonates and/or alkyl carbamates by thin-film evaporation at from 180° C. to 250° C., and a pressure of from 0.1 mbar to 20 mbar.

27. The multistage process of claim 25, wherein, in the second stage of (b), the liquid effluent is freed of any residual alcohol present and also middle boilers such as dialkyl carbonates and/or alkyl carbamates by thin-film evaporation at from 180° C. to 250° C., and a pressure of from 0.1 mbar to 20 mbar.

28. The multistage process of claim 2, wherein the vapors of (b) are fed, after further distillative purification, into (a).

29. The multistage process of claim 2, wherein (c) is carried out at a temperature of from 180 to 260° C., and under a pressure of from 0.01 to 10 mbar.

30. The multistage process of claim 2, wherein (c) is carried out using a thin-film or short-path evaporator.

31. The multistage process of claim 2, wherein the by-products from (c) are discharged and discarded.

32. The multistage process of claim 2, wherein the stream in (b) is not processed as per stage (c), but rather is divided before its distillative purification into two substreams of which one substream is fed directly to the cleavage reaction (d).

33. The multistage process of claim 2, wherein (d) is carried out in a combined cleavage and rectification column.

34. The multistage process of claim 2, wherein, in (d), thermal cleavage is effected continuously at temperatures of from 180 to 280° C., and under a pressure of from 0.1 to 200 mbar.

35. The multistage process of claim 2, wherein, in (d), thermal cleavage is effected continuously at temperatures of from 180 to 280° C., and under a pressure of from 0.1 to 200 mbar.

36. The multistage process of claim 2, wherein, in (d), cleavage is effected without solvent in the liquid phase.

37. The multistage process of claim 2, wherein (d) is carried out in the presence of a catalyst.

38. The multistage process of claim 2, wherein the thermally induced diurethane cleavage of (d) is carried out in a tubular furnace or an evaporator.

39. The multistage process of claim 2, wherein, in (d), the conversion of diurethane to diisocyanate is selected freely depending on the diurethane used.

40. The multistage process of claim 2, wherein, in (d), a portion of the reaction mixture which comprises unconverted diurethanes, high-boiling by-products and other reutilizable and nonutilizable by-products is continuously discharged.

41. The multistage process of claim 30, wherein the amount of the discharge is from 10 to 60% by weight, based on the feed.

42. The multistage process of claim 2, wherein (e) is carried out in a combined cleavage and rectification column.

43. The multistage process of claim 2, wherein (e) is effected at a temperature of from 95 to 260° C., and a pressure of from 0.5 to 250 mbar.

44. The multistage process of claim 2, wherein the crude fraction obtained from (e), consisting of cycloaliphatic diisocyanate, partially cleaved cycloaliphatic diurethane and in some cases small fractions of cycloaliphatic diurethane, is purified in (f) by distilling at a temperature of from 95 to 260° C., and under a pressure of from 0.5 to 150 mbar.

45. The multistage process of claim 44, wherein the fraction obtained in (f) is isolated as a pure product or recycled into (g).

46. The multistage process of claim 2, wherein (g) is carried out in a continuous tank battery or in a tubular reactor.

47. The multistage process of claim 2, wherein the reaction in (g) is effected in the presence of one or more catalysts selected from the group consisting of tin carboxylates, tin halides, zinc carboxylates, zinc halides and tertiary amines.

48. The multistage process of claim 2, wherein the recycling in (h) is into (g).

49. The multistage process of claim 2, wherein, in (h), the amount of the discharge is from 0.1 to 50% by weight, of the feed of crude polyisocyanate into the purifying distillation (f).

50. The multistage process of claim 2, wherein the amount of top fraction removed per unit time in (i) is from 0.1 to 3% by weight, of the feed of crude diisocyanate into the purifying distillation (f)).

51. The multistage process of claim 2, wherein Fe(III) chloride, Fe(III) bromide, Cu(I) chloride and Cu(I) bromide are used in (k).

52. The multistage process of claim 1, wherein 1,4-diisocyanatocyclohexane, 4,4'-dicyclohexylmethane diisocyanate, 2,2'-dicyclohexylmethane diisocyanate, 2,4'-dicyclohexylmethane diisocyanate or else any mixtures of at least two isomeric dicyclohexylmethane diisocyanates are prepared.

53. The multistage process of claim 2, wherein 1,4-diisocyanatocyclohexane, 4,4'-dicyclohexylmethane diisocyanate, 2,2'-dicyclohexylmethane diisocyanate, 2,4'-dicyclohexylmethane diisocyanate or else any mixtures of at least two isomeric dicyclohexylmethane diisocyanates are prepared.

54. A method according claim 1, wherein the diamine is at least one selected from the group consisting of 1,3- and 1,4-diaminomethylcyclohexane, hexanediamine-1,6,2,2,4- or 2,4,4-trimethylhexaneamine-1,6 and 3-aminomethyl-3,5,5-trimethylcycohexylamine.

* * * * *